US006911339B2

(12) United States Patent
Dumas

(10) Patent No.: US 6,911,339 B2
(45) Date of Patent: Jun. 28, 2005

(54) TRANSPARENT POLYMER SUPPORT FOR ORGANIC SYNTHESIS

(76) Inventor: David P. Dumas, 15803 Caminito Cercado, San Diego, CA (US) 92128

(*) Notice: Subject to any disclaimer, the term of this patent is extended or adjusted under 35 U.S.C. 154(b) by 279 days.

(21) Appl. No.: 10/118,556

(22) Filed: Apr. 8, 2002

(65) Prior Publication Data
US 2003/0013188 A1 Jan. 16, 2003

Related U.S. Application Data
(60) Provisional application No. 60/282,691, filed on Apr. 9, 2001.

(51) Int. Cl.$^7$ ................................................ C12M 1/00
(52) U.S. Cl. ........................ 435/283.1; 435/287.2; 435/288.1; 435/288.3; 435/288.4; 435/304.1; 435/304.3; 435/305.1; 422/99; 422/102
(58) Field of Search ................ 422/99, 102; 435/283.1, 435/287.2, 288.1, 288.3, 288.4, 304.1, 304.3, 305.1

(56) References Cited

U.S. PATENT DOCUMENTS

| | | | |
|---|---|---|---|
| 2,370,565 A | 2/1945 | Muskat et al. ................ 260/78 |
| 2,370,567 A | 2/1945 | Muskat et al. ............... 260/463 |
| 2,385,933 A | 10/1945 | Muskat et al. ................ 260/78 |
| 2,403,113 A | 7/1946 | Muskat et al. ................ 260/78 |
| 2,407,446 A | 9/1946 | Pollack et al. ................ 260/78 |
| 2,464,056 A | 3/1949 | Pechukas .................... 260/463 |
| 2,587,437 A | 2/1952 | Bralley et al. ............... 260/77.5 |
| 3,385,836 A | 5/1968 | Mednick et al. ............. 260/78.4 |
| 3,751,374 A | 8/1973 | Berry et al. ................. 260/17.4 |
| 4,083,819 A | 4/1978 | Hisano et al. ............... 528/503 |
| 4,139,578 A | 2/1979 | Baughman et al. ........... 525/39 |
| 4,311,762 A | 1/1982 | Spycher et al. .............. 428/412 |
| 4,346,197 A | 8/1982 | Crano et al. ................. 525/277 |
| 4,396,737 A | 8/1983 | Leatherman ................. 524/176 |
| 4,398,008 A | 8/1983 | Misura ........................ 526/314 |
| 4,590,248 A | 5/1986 | Moriya et al. ............... 526/228 |
| 4,613,656 A | 9/1986 | Tang ........................... 526/193 |
| 4,622,376 A | 11/1986 | Misura et al. ............... 526/286 |
| 4,686,266 A | 8/1987 | Tang ........................... 526/193 |
| 4,735,832 A * | 4/1988 | Ichikawa et al. ............ 428/36.6 |
| 4,959,429 A | 9/1990 | Misura et al. ............... 526/230.5 |
| 4,959,433 A | 9/1990 | Oates et al. ................. 526/314 |
| 5,017,666 A | 5/1991 | Crano et al. ................ 526/230.5 |
| 5,143,854 A | 9/1992 | Pirrung et al. ............... 436/518 |
| 5,173,552 A | 12/1992 | Renzi et al. ................. 526/230.5 |
| 5,200,483 A | 4/1993 | Selvig ......................... 526/301 |
| 5,624,711 A | 4/1997 | Sundberg et al. ............ 427/261 |
| 5,910,287 A | 6/1999 | Cassin et al. ................ 422/102 |
| 6,057,411 A | 5/2000 | Herold ........................ 526/314 |

FOREIGN PATENT DOCUMENTS

WO  WO 98/55231  12/1998
WO  WO 00/55627   9/2000

OTHER PUBLICATIONS

Andres et al., "Recent advances in the solid phase synthesis of drug–like heterocyclic small molecules," Comb. Chem. High Throughput Screen. 2:191–210 (1999).
Beaucage and Iyer, "Advances in the synthesis of oliognucleotides by the phosphoramidite approach," Tetrahedron Lett. 48:2223–2311 (1992).
Fields and Noble, "Solid phase peptide synthesis utilizing 9–fluorenylmethoxycarbonyl amino acids," Int. J. Peptide Protein Res. 35:16 (1990).
Freemantle, "Chemical analysis and synthesis on microchips promise a variety of potential benefits," Chem. Eng. News 77:27–36 (1999).
Gryaznov and Letsinger, "A new approach to synthesis of oligonucleotides with 3' phosphoryl groups," Tetrahedron Lett. 33:4127–4128 (1992).
Koch et al., Microfluidic Technology and Applications, Research Studies Press Limited, Baldock, Hertfordshire, England (2000).
Lockhart and Winzeler, "Genomics, gene expression and DNA arrays," Nature 405:827–836 (2000).
Manz, ed., Microsystem Technology in Chemistry and Life Sciences, Springer–Verlag, New York (1999).
McGall et al., "The efficiency of light–directed synthesis of DNA arrays on glass substrates," J. Amer. Chem. Soc. 119:5081–5090 (1997).
Montserrat et al., "Criteria for the economic large scale solid–phase synthesis of oligonucleotides," Tetrahedron 50:2617–2622 (1994).
Backes and Ellman, "Solid support linker strategies," Curr. Opin. Chem. Biol. 1:86–93 (1997).
Becker and Gartner, "Polymer microfabrication methods for microfluidic analytical applications," Electrophoresis 21:12–26 (2000).
Blackburn and Kates, "Solid–phase synthesis of cyclic homodetic peptides," Methods Enzmol. 289:175–198 (1997).
Chován and Guttman, "Microfabricated devices in biotechnology and biochemical processing," Trends Biotechnol. 20:116–122 (2002).

(Continued)

Primary Examiner—David A. Redding
(74) Attorney, Agent, or Firm—McDermott Will & Emery LLP

(57) ABSTRACT

The invention provides polyol (allyl carbonate) polymer solid supports. The supports can be modified for attachment of a chemical moiety or ligand. A solid support comprising one or more ligands immobilized to a polyol (allyl carbonate) polymer solid support. The solid support can be in the form of a bead, fiber, flat surface, microfluidic device, molded device, machined device, container, multi-well container such as a multi-well plate, and mass spectrometry sample holder. The solid supports can be used for a variety of applications, including chemical storage, chemical synthesis, combinatorial library synthesis, analytical devices, diagnostic devices, and tissue culture applications. The invention also provides methods of using the polyol (allyl carbonate) polymer solid supports.

36 Claims, No Drawings

OTHER PUBLICATIONS

DeWitt, "Microreactors for chemical synthesis," *Curr. Opin. Chem Biol.* 3:350–356 (1999).

Fodor et al., "Light–directed, spatially addressable parallel chemical synthesis," *Science* 251:767 (1991).

Gallop et al., "Applications of combinatorial technologies to drug discovery. 1. Background and peptide combinatorial libraries," *J. Med. Chem.* 37:1233–1251 (1994).

Gordon et al., "Applications of combinatorial technologies to drug discovery. 2. Combinatorial organic synthesis, library screening strategies, and future directions," *J. Med. Chem.* 37:1385–1401 (1994).

Ito and Manabe, "Solid–phase oligosaccharide synthesis and related technologies," *Curr. Opin. Chem. Biol.* 2:701–708 (1998).

Kihlberg et al., "Direct synthesis of glycosylated amino acids from carbohydrate peracetates and Fmoc amino acids: solid–phase synthesis of biomedicinally interesting glycopeptides," *Methods Enzymol.* 289:221–245 (1997).

Krishnan et al., "Microfabricated reaction and separation systems," *Curr. Opin. Biotechnol.* 12:92–98 (2001).

Labadie, "Polymeric supports for solid phase synthesis," *Curr. Opin. Chem. Biol.* 2:346–352 (1998).

Matson et al., "Biopolymer synthesis on polypropylene supports. I. Oligonucleotides," *Anal. Biochem.* 217:306–310 (1994).

Meldal, "Properties of solid supports," *Methods Enzymol.* 289:83–104 (1997).

Mendonca and Xiao, "Optimization of solid supports for combinatorial chemical synthesis," *Med. Res. Rev.* 19:451–462 (1999).

Merrifield, "Concept and early development of solid–phase peptide synthesis," *Methods Enzymol.* 289:3–13 (1997).

Sucholeiki, "New developments in solid phase synthesis supports," *Mol. Divers.* 4:25–30 (1998–1999).

Thuong and Asseline, "Chemical synthesis of natural and modified oligodeoxynucleotides," *Biochimie.* 67:673–684 (1985).

van Maarseveen, "Solid phase synthesis of heterocycles by cyclization/cleavage methodologies," *Comb. Chem. High Throughput Screen.* 1:185–214 (1998).

Voldman et al., "Microfabrication in biology and medicine," *Ann. Rev. Biomed. Eng.* 1:401–425 (1999).

Wang et al., "Identification of a blue photoluminescent composite material from a combinatorial library," *Science* 279:1712–1714 (1998).

* cited by examiner

TRANSPARENT POLYMER SUPPORT FOR ORGANIC SYNTHESIS

This application claims benefit of the filing date of U.S. Provisional Application No. 60/282,691, filed Apr. 9, 2001, which is incorporated herein by reference.

BACKGROUND OF THE INVENTION

The present invention relates generally to polymers and more specifically to polymers having useful optical and chemical resistance properties.

With the wealth of genetic information available from genome projects, focus has centered on the analysis of arrays of genes and proteins. Experimentally, this analysis is made possible with the development of microarray technologies where thousands or tens-of-thousands of genes are surveyed with a single biochip. Leading biochip technologies are the DNA-based chips, with protein chips being developed only recently.

Biochips have been constructed using both deposition techniques and by synthesis of the biopolymer (DNA or peptide) directly on the solid support. Both glass and nylon membranes have been used as solid supports for DNA-based chips (Lockhart and Winzeler *Nature,* 405:827–836 (2000)). Of these, glass allows greater density arrays and more flexibility for detection. In particular, fluorescence techniques have been used to interrogate DNA arrays. DNA-based biochips are constructed using either deposition of DNA onto aminosilane or poly-lysine coated slides or by direct synthesis of the DNA on derivatized glass using light-directed synthesis (Sundberg and Fujimoto, U.S. Pat. No. 5,624,711 (1997)).

Noncovalent depostion of the DNA on the chip allows the flexibility to generate custom biochips. However, the random orientation of the DNA on the surface can reduce sensitivity, and the absence of covalent attachment prevents the reuse of the chips. Covalent attachment of DNA to glass slides and silicon wafer was made possible by methods developed at Affymetrix (Pirrung et al., U.S. Pat. No. 5,143,854 (1992)). Glass slides modified with silicon derivatives are used as a support for light-directed synthesis using projection masks similar to those used in the photolithographic etching of computer chips. For the synthesis of a single 20-mer chip, eighty different masks are necessary. The high cost for producing each mask makes this method most suitable for the production of multiple copies of the same oligonucleotide array. Additionally, many of these solid supports have performance problems including pH instability, poor physical strength, solvent incompatability, chemical reactivity, and nonspecific absorption of biomolecules. As the result of instability to reagents used in chemical regeneration, biochips synthesized on these supports are not reusable. As an alternative to glass and silicon supports, polypropylene has been proposed (Matson et al., *Anal. Biochem.* 217: 306–310 (1994)). While polypropylene provides many advantages over glass in terms of chemical and solvent stability and physical strength, the poor optical properties and flexibility of the plastic make polypropylene unsuitable for most array applications.

The development of biochips has followed a trend of miniaturization in the biotechnology and pharmaceutical industries whereby reagent costs and analysis speeds are minimized through the reduction of assay volumes. This miniaturization is especially apparent in high throughput screening where 96-well, 384-well, and 1536-well plates with assay volumes of 400 μL to 1 μL, respectively, are in routine use. The microwell plates are conventionally made from clear, white, or black plastic, such as polypropylene, polystyrene, or acrylonitrile-butadiene-styrene (ABS) that has relatively low intrinsic fluorescent properties. The use of microwell plates also permits very dense storage of collectives of discrete compounds for later testing as films in addressable grid positions, thus reducing the number of handling steps for the analysis of a collection of compounds.

Microwell plates have also been used in combinatorial chemistry where organic and inorganic compounds are synthesized directly in the microwells in solution, on beads, or on the microwell surface itself. As a result of the many solvents and reagents used in combinatorial chemistry, these microwell plates have essentially been limited to polypropylene. Polypropylene, an opaque thermoplastic, has poor hardness and flexibility characteristics that lead to deformation and inaccuracies in the final molded product. Consequently, it would be desirable to provide a polymeric support material that is transparent, shows low fluorescence, and is resistant to organic solvents that can be used for the construction of biochips, microwell plates and other solid supports that allow increased throughput screening by incorporating a large number of small wells.

Thus, there exists a need for a solid support having optical properties and chemical stability suitable for chemical synthesis. The present invention satisfies this need, and provides related advantages as well.

SUMMARY OF THE INVENTION

The invention provides polyol (allyl carbonate) polymer solid supports. The supports can be modified for attachment of a chemical moiety or ligand. A solid support comprising one or more ligands immobilized to a polyol (allyl carbonate) polymer solid support. The solid support can be in the form of a bead, fiber, flat surface, microfluidic device, molded device, machined device, container, multi-well container such as a multi-well plate, and mass spectrometry sample holder. The solid supports can be used for a variety of applications, including chemical storage, chemical synthesis, combinatorial library synthesis, analytical devices, diagnostic devices, and tissue culture applications. The invention also provides methods of using the polyol (allyl carbonate) polymer solid supports.

DETAILED DESCRIPTION OF THE INVENTION

The invention provides polyol (allyl carbonate) polymer solid supports having properties useful for a variety of applications, including chemical synthesis, and methods of making and using the solid supports. The solid supports of the invention are advantageous in that they have high clarity, low intrinsic fluorescence, resistance to a variety of chemical solvents, and can be chemically modified to allow attachment of a chemical moiety. The solid supports of the invention are transparent organic polymer supports, which are particularly useful in organic synthesis, allowing for highly efficient solid phase synthesis. Thus, the solid supports of the invention are especially useful in the preparation of biochips and synthesis of combinatorial compound libraries.

As used herein, a "ligand" refers to a molecule that can specifically bind to a binding partner. The term specifically means that the binding interaction is detectable over non-specific interactions by a quantifiable assay. A ligand can be essentially any type of molecule such as a peptide or polypeptide, nucleic acid or oligonucleotide, carbohydrate such as oligosaccharides, an organic derived compound, or an inorganic derived compound.

As used herein, the term "polypeptide" refers to a peptide, polypeptide or protein of two or more amino acids. A polypeptide can also be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

A modification of a peptide can also include non-naturally occurring derivatives, analogues and functional mimetics thereof generated by chemical synthesis. Derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

As used herein, the term "nucleic acid" or "oligonucleotide" means a polynucleotide such as deoxyribonucleic acid (DNA) or ribonucleic acid (RNA). A nucleotide incorporated into an oligonucleotide can be a naturally occurring nucleotide or non-naturally occurring nucleotide, including derivatives thereof such as phosphoramidates and the like. Such derivatized molecules include analogs of adenosine, substituted adenosines, ethenoadenosine, guanosine, substituted guanosines, inosine, substituted inosines, uridine, 5,6-dihydrouridine, substituted uridines, cytodine, substituted cytodines, thymidine, substituted thymidines, and the like. Derivatized molecules also include glycosylated derivatives of purines, pyrimidines, imidazoles, pyridines, pyrollopyrimidines, pyrazallopyrimidine, pyroles, and other nitrogen containing heterocycles. Derivatized molecules also include modifications of the sugar group to include pentoses, substituted pentoses, deoxy-pentoses, hexoses, substituted hexoses, deoxy-hexoses, and the like.

As used herein, the term "oligosaccharide" refers to polymers of monosaccharides that can be linear or branched. Oligosaccharides include modifications of monosaccharides. As used herein, the term "organic molecule" refers to organic molecules that are chemically synthesized or are natural products. As used herein, the term "inorganic molecule" refers to inorganic molecules that are chemically synthesized or are natural products.

As used herein, a "polyol (allyl carbonate)" polymer refers to a polymerizate of organic composition based on a radically polymerizable monomer represented by the general formula:

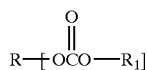

where R is a polyol having two or more hydroxy groups and $R_1$ is an allyl or substituted allyl group. Polyol (allyl carbonate) polymers useful in the invention include homopolymers or copolymers that include mono-functional allyl carbonates, diol bis(allyl carbonates), trial tris(allyl carbonates), tetra kis(allyl carbonates), higher polyol (allyl carbonates), and the like.

As used herein, a "solid support" refers to any configuration of a solid polymer. For example, a solid support can be in the form of a bead, fiber, planar surface, molded device, machined device, container, multi-well container such as a multi-well plate, or a mass spectrometry (MS) sample holder. It is particularly useful for the solid support to be in a configuration suitable for attaching one or more chemical moieties, for example, for chemical synthesis, or for use in tissue culture applications.

As used herein, "immobilized," "immobilizing," and other grammatical forms refers to the stable attachment to a solid support of a chemical moiety such as a ligand. A ligand or chemical moiety can be immobilized via covalent or non-covalent interactions so long as the attached molecule is stable under the conditions of use of the solid support. For example, if the use of the solid support involves washing with a solvent to remove unattached chemical moieties, an immobilized chemical moiety remains attached to the solid support in the wash conditions used for a particular purpose. One skilled in the art can readily determine whether a chemical moiety remains immobilized to a solid support using well known methods of detecting the presence of a chemical moiety. Such methods can involve directly testing for the presence of a chemical moiety on a solid support or the removal or cleavage of the ligand or chemical moiety from the solid support to test for its presence, if desired, as exemplified below (see Example IV).

The invention provides a polyol (allyl carbonate) polymer support in a variety of configurations, particularly those suitable for chemical synthesis or tissue culture applications. Polymers of allyl carbonate have particularly useful optical properties in that they are colorless and clear. Such polymers of polyol (allyl carbonate) are also abrasion, chemical, heat, and radiation resistant. Polymers of allyl carbonate have found use as transparent coatings, optical lenses, optical lens blanks, other optical elements, and transparent flat and curved sheets. Plastics cast from diethylene glycol bis(allyl carbonate) monomers can be fabricated using standard machining operations, and cast sheets can be hot formed into a variety of shapes.

One problem associated with the polymerization of polyol (allyl carbonate)-functional monomer compositions is the relatively high shrinkage of the material that occurs during the course of polymerization to the final thermoset polymer. For example, there is a shrinkage of approximately 13 percent during the polymerization of diethylene glycol bis (allyl carbonate). Such high shrinkages are particularly detrimental in casting operations where the liquid monomer composition is introduced into a mold and thereafter polymerized to the final thermoset polymer.

It is known that introducing a liquid prepolymer into the mold and thereafter polymerizing the prepolymer to the final thermoset polymer results in a decrease in shrinkage in the mold. The prepolymer is usually produced by partially polymerizing the polyol (allyl carbonate)-functional monomer composition to consume a portion of the allylic groups. For example, the prepolymer can comprise diethylene glycol bis(allyl carbonate), which is partially polymerized. The partial polymerization is stopped before more than a trivial amount of gellation occurs so that the prepolymer can be introduced into the mold as a liquid. The partially polymerized liquid polymer has about 20 to 50% allylic utilization and is a syrupy, substantially gel-free, pourable viscous liquid of unpolymerized monomer and polymer. Prepolymerization of polyol (allyl carbonate)-functional monomer compositions have been described by PPG Industries (U.S. Pat. Nos. 4,613,656, 4,686,266, 4,959,429, 4,959,433, 5,017,666 and 6,057,411, each of which is incorporated herein by reference). Additional methods for generating polymers of the invention are described in U.S. Pat. Nos. 4,346,197, 4,396,737, 4,398,008, 4,590,248 and 4,622,376, each of which is incorporated herein by reference. If desired, the solid support can be generated by polymerizing a prepolymer of polyol (allyl carbonate). Polyol (allyl carbonate)-functional monomer compositions can therefore be readily molded into shapes convenient for combinatorial chemistry, particularly for biochips and microwell plates.

Diol bis(allyl carbonate) monomers are normally linearly polymerized aliphatic liquid allyl carbonates, that is, glycol bis(allyl carbonate) compounds, in which the allyl groups can be substituted at the 2 position with a halogen, notably chlorine or bromine, or a 1 to 4 carbon alkyl group, generally a methyl or ethyl group, and the glycol group can be an alkylene, alkylene ether, alkylene polyether or alkylene carbonate group having from 2 to 10 carbons and oxygens. These diol bis(allyl carbonate) monomers are represented by the formula:

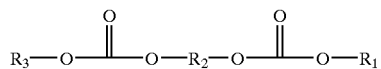

where $R_1$ and $R_3$ are allyl or substituted allyl groups, and $R_2$ is as defined below. $R_1$ and $R_3$ are independently represented by the formula:

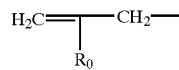

where $R_0$ can be hydrogen, halogen, or a 1 to 4 carbon alkyl group. Specific examples of $R_1$ and $R_3$ include allyl, 2-chloroallyl, 2-bromoallyl, 2-iodoallyl, 2-fluoroallyl, 2-methallyl, 2-ethylallyl, 2-isopropylallyl, 2-n-propylallyl, and 2-n-butylallyl groups. Most commonly, $R_1$ and $R_3$ are allyl groups, $H_2C=CH—CH_2—$. Such compounds and methods for making them are disclosed in U.S. Pat. Nos. 2,370,567 and 2,403,113, each of which is incorporated herein by reference.

Specific examples of $R_2$ include alkylene groups containing from 2 to 10 carbons such as ethylene, trimethylene, methylethylene, tetramethylene, ethylethylene, pentamethylene, hexamethylene, 2-methylhexamethylene, octamethylene, and decamethylene groups, alkylene ether groups such as —$CH_2$—O—$CH_2$—, —$CH_2CH_2$—O—$CH_2CH_2$—, —$CH_2$—O—$CH_2$—$CH_2$—, and —$CH_2CH_2CH_2$—O—$CH_2CH_2CH_2$—, alkylene polyether groups such as —$CH_2CH_2$—O—$CH_2CH_2$—O—$CH_2CH_2$—O—$CH_2CH_2$O—$CH_2CH_2$—, and —$CH_2$—O—$CH_2$— groups, and alkylene carbonate and alkylene polycarbonate groups such as $CH_2CH_2$—O—CO—O—$CH_2CH_2$ and —$CH_2CH_2$—O—$CH_2CH_2$—O—CO—O—$CH_2CH_2$—O$CH_2CH_2$— groups. Most commonly, $R_2$ is —$CH_2CH_2$—, —$CH_2CH_2$—O—$CH_2CH_2$—, or —$CH_2CH_2$—O—$CH_2CH_2$—O—$CH_2CH_2$.

Specific examples of polyol (allyl carbonate) monomers useful in carrying out the method herein contemplated include ethylene glycol bis (2-chloroallyl carbonate), diethylene glycol bis (2-methallyl carbonate), triethylene glycol bis (allyl carbonate), propylene glycol bis (2-ethylallyl carbonate), 1,3-propanediol bis (allyl carbonate), 1,3-butanediol bis (allyl carbonate), 1,4-butanediol bis (2-bromoallyl carbonate), dipropylene glycol bis (allyl carbonate), trimethylene glycol bis (2-ethylallyl carbonate), pentamethylene glycol bis (allyl carbonate), isopropylidene bisphenol bis(allyl carbonate), oxy bisphenol bis(allyl carbonate), sulfonyl bisphenol bis(allyl carbonate), and the tris(allyl carbonate) of tris(2-hydroxyethyl)isocyanurate.

Commercially important polyol (allyl carbonate) monomers which can be polymerized for the invention herein contemplated are:

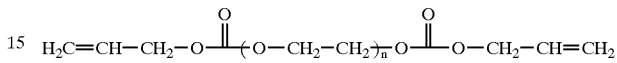

where n=1 to 3. A particularly useful polyol (allyl carbonate) is diethylene glycol bis(allyl carbonate). This monomer is commercially available from PPG Industries, Inc. and is sold under the trademark CR-39 Allyl Diglycol Carbonate™ (PPG Industries; Gurnee Ill.).

In addition to the above-described references, methods describing the use of triol (allyl carbonates) and other polymeric forms described below can be found, for example, in U.S. Pat. Nos. 2,370,565, 2,370,567, 2,385,933, 2,403, 113, 2,407,446, 2,464,056, 2,587,437, 3,385,836, 3,751,374, 4,083,819, 4,139,578, 4,311,762, and 4,346,197, each of which is incorporated herein by reference.

Triol tris(allyl carbonates) that can be polymerized and are useful in the invention are represented by the formula:

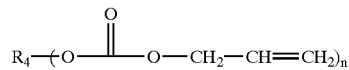

where $R_4$ is an organic moiety chosen from the group consisting of moieties derived from polyols and extended polyols, most frequently a triol or extended triol where the hydroxyl groups of the precursor polyol $R_4(OH)_n$ are non-vicinal. Such triol tris(allyl carbonates) can be either homopolymerized or copolymerized, for example, with polyol (allyl carbonates) such as diol bis(allyl carbonates).

By non-vicinal it is meant that the hydroxyl groups are not on adjacent carbons. Specific triol precursors useful in preparing the tris(allyl carbonate) materials useful in this invention are triols with primary or secondary hydroxyl groups. Triols having primary hydroxyl groups are particularly useful precursors. One such class of triols are 1,1,1-trimethylol alkanes. Also useful are extended trimethylol alkale tris(allyl carbonate) monomers such as lactone extended trimethylol alkanes and alkyl oxide extended trimethylol alkanes. By an extended triol is meant the reaction product having terminal hydroxyl groups of the triol and a suitable reactant, for example, an alkyl oxide or a lactone. Typical lactone extended trimethylol alkanes include ε-caprolactone extended trimethylol methane, ε-caprolactone extended trimethylol ethane, ε-caprolactone extended trimethylol propane, and ε-caprolactone extended trimethylol butane. Typical alkyl oxide extended triols include ethylene oxide extended trimethylol methane, ethylene oxide extended trimethylol ethane, ethylene oxide extended trimethylol propane, ethylene oxide extended trimethylol butane, propylene oxide extended trimethylol methane, propylene oxide extended trimethylol methane, propylene oxide extended trimethylol ethane, and propylene oxide extended trimethylol butane.

Particularly useful polyols meeting these requirements have the general formula $R_5(OH)_n$, where n is greater than 2, up to about 8 and generally is about 3. $R_5$ can be:

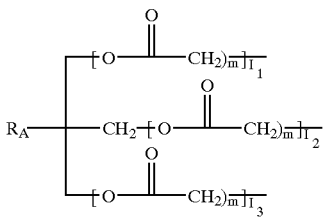

where $R_A$ is H, —$CH_3$, —$CH_2CH_3$, —$CH_2CH_2CH_3$, or —$CH_2CH_2C_3$ and $I_1$, $I_2$ and $I_3$ are each integers from 0 to 5 and the sum of $I_1+I_2+I_3$ is 2 or more and generally from 2 to 8, although values as high as 15 are possible. The value of m depends on the lactone utilized to extend the polyol and is generally 4 or 5.

The chain extending lactone can be a delta lactone having the formula:

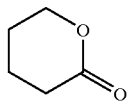

which can be substituted with hydrogen, methyl groups, or ethyl groups.

According to a still further exemplification, the chain extending lactone group can be an epsilon lactone having the formula:

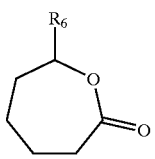

where $R_6$ is hydrogen, a methyl group, or an ethyl group and where $R_5$ can be on any of the carbons other than the carbonyl carbon. One exemplary triol is Union Carbide Corporation NIAX™ PCP-0301 brand epsilon-caprolactone extended trimethylol propane (Union Carbide/DOW Chemical Co.; Midland Mich.).

According to a still further exemplification, $R_5$ can be:

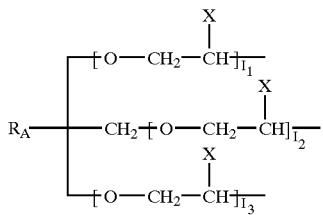

where $R_A$ is as defined above, $I_1$, $I_2$ and $I_3$ are integers from 0 to 5 and the sum of $I_1+I_2+I_3$ is 2 or more and generally from about 2 to 8, although values as high as about 15 are possible, and X is H or $CH_3$. The chain extenders can be ethylene oxide groups as exemplified by Upjohn ISONOL™ 93 ethylene oxide extended trimethylol propane (Pharmacia & Upjohn; Peapack N.J.). Alternatively, the extenders can be propylene oxide groups as in BASF-Wyandotte PLURACOL TP brand propoxylated trimethylol propane (BASF; Mount Olive N.J.).

According to a still further exemplification, $R_5(OH)_3$ can be an extended glycerol, for example, ethylene oxide extended glycerol having the general formula:

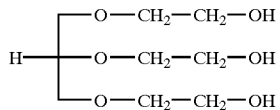

or propylene oxide extended glycerol having the formula:

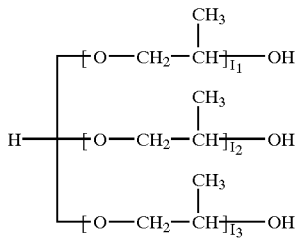

or a lactone extended glycerol having the formula:

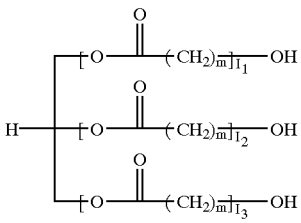

where m and $I_1$, $I_2$, and $I_3$ are as defined above. Typical propoxylated glycerines include DOW VORANOL 2025 brand propoxylated glycerine having a molecular weight of about 260 grams per gram mole (DOW Chemical Co.), DOW VORANOL 2070 brand propoxylated glycerine having a molecular weight of about 700 grams per gram mole (DOW Chemical Co.), and BASF-Wyandotte PLURACOL GP730 brand propoxylated glycerine having a molecular weight of about 730 grams per gram mole (BASF).

Other monomeric or polymeric materials can be introduced into the monomeric polyol (allyl carbonate) and polymerized therewith. These materials can be added to alter viscosity of the polyol (allyl carbonate) while monomeric, thereby making processing easier. For example, olefinically unsaturated monomers, such as ethylene, propylene, isobutylene, methylpentene, butadiene, isoprene, vinyl acetate, acrylic acid, methacrylic acid, methyl acrylate, ethyl acrylate, methyl methacrylate, ethyl methacrylate, acrylonitrile, acrylamide, vinyl chloride, vinylidene chloride, vinyl pyrrolidene, vinyl pyridene, vinyl-methyl ether, vinyl ethyl ether styrene, divinyl benzene, and mixtures thereof can be introduced into the monomeric polyol (allyl carbonate) and co-polymerized. Alternatively, allyl monomers, such as allyl alcohol, can be introduced into the monomeric polyol (allyl carbonate), or even monomers having allyl and vinyl functionality, such as allyl methacrylate or allyl acrylate, can be introduced into the polyol (allyl carbonate).

Alternatively a polymeric material can be introduced into the polyol (allyl carbonate) monomer. Exemplary polymers that can be co-polymerized with a polyol (allyl carbonate) polymer are described below.

As herein contemplated, the polymer can be a monofunctional homopolymer or a copolymer of monofunctional monomers, or a copolymer of a monofunctional monomer and a difunctional monomer. When the polymer is a polymer of a difunctional monomer, or a copolymer of a monofunctional monomer and a difunctional monomer, the difunctional monomer can have functional groups of high and low reactivity, for example, a vinyl group and an allyl group, and the monofunctional monomer can be a vinyl monomer.

A particularly useful copolymer is a copolymer of (a) an acrylate, that is, an acrylate ester or an acrylic acid, and (b) an ester of an acrylic acid and an allyl alcohol or substituted allyl alcohol. The difunctional monomer can be allyl acrylate, allyl methacrylate, or the like, and the monofunctional monomer can be methyl acrylate, methyl methacrylate, ethyl acrylate, ethyl methacrylate, or the like. In this way there is provided a linear, minimally cross linked, soluble, swellable polymer, with polymerization predominantly through the vinyl groups.

Alternatively, the polymer can be a polymer of a monomer having mono-olefinic unsaturation, for example, poly(styrene), poly(acrylonitrile), poly(vinyl chloride), poly(vinylidene chloride), poly(vinyl fluoride), poly(vinylidene fluoride), poly(vinyl acetate), poly(acrylic acid), poly(methacrylic acid), poly(methyl acrylate), poly(ethyl acrylate), poly(butyl acrylate), poly(methyl methacrylate), poly(ethyl methacrylate), poly(butyl methacrylate), poly(acrylamide), poly(ethylene), poly(propylene), poly(allyl acrylate), poly(allyl methacrylate), and copolymers thereof. Alternatively, the polymer can be a heterochain polymer, that is, a condensation polymer. Suitable heterochain polymers include saturated polyesters such as terephthalates, for example, polyethylene terephthlate, and polycarbonates; polyethers, such as polyacetal, poly(ethylene oxide), poly(propylene oxide), poly(epichlorohydrin), poly(epichlorohydrin-ethylene oxide), poly(tetrahydrofuran); or polyamides and polyimides.

Particularly useful polymers are homopolymers of diethylene glycol bis(allyl carbonate) or copolymers containing about 10% or more of diethylene glycol bis (allyl carbonate). In addition, a copolymer can contain about 15% or more of diethylene glycol bis(allyl carbonate), about 20% or more of diethylene glycol bis(allyl carbonate), about 25% or more of diethylene glycol bis(allyl carbonate), about 30% or more of diethylene glycol bis(allyl carbonate), about 35% or more of diethylene glycol bis(allyl carbonate), about 40% or more of diethylene glycol bis(allyl carbonate), about 45% or more of diethylene glycol bis(allyl carbonate), about 50% or more of diethylene glycol bis(allyl carbonate), about 60% or more of diethylene glycol bis(allyl carbonate), about 70% or more of diethylene glycol bis(allyl carbonate), about 80% or more of diethylene glycol bis(allyl carbonate), about 90% or more of diethylene glycol bis(allyl carbonate), or about 95% or more of diethylene glycol bis(allyl carbonate). Similarly, other polyol (allyl carbonate) polymers can be synthesized as co-polymers of variable percentages, as described above, for example, about 10%, about 15%, about 20%, about 25%, about 30%, about 35%, about 40%, about 45%, about 50%, about 60%, about 70%, about 80%, about 90% or about 90% polyol (allyl carbonate).

In addition to the above-described copolymers, a solid support of the invention can also be made by applying a polyol (allyl carbonate) coating to a solid support. Accordingly, the invention provides a solid support comprising a polyol (allyl carbonate) polymer, where the polymer is coated onto a solid support. For example, the polyol (allyl carbonate) polymer can be coated onto a polystyrene, polypropylene, or any desired solid support useful in methods of the invention.

Additionally, colorants can be present in the monomer, whereby to provide a colorant in the casting.

The polymerization of the polyol (allyl carbonate) composition is initiated by the creation of active centers, for example, free radicals. Useful free radical initiators are peroxy initiators. The peroxy initiators include: isobutyryl peroxide; di(2-ethylhexyl) peroxydicarbonate; acetyl cyclohexane sulfonyl peroxide; di(sec-butyl) peroxydicarbonate; diisopropyl peroxydicarbonate; 2,4-dichlorobenzoyl peroxide, t-butyl peroxypivalate; decanoyl peroxide; lauroyl peroxide, propionyl peroxide; 2,5-dimethyl-2,5-bis(2-ethyl hexylperoxy) hexane; acetyl peroxide; succinic acid peroxide; t-butyl peroxyoctoate; benzoyl peroxide; p-chlorobenzoyl peroxide; t-butyl peroxyisobutyrate; t-butyl peroxymaleic acid; bis(1-hydroxycyclohexyl) peroxide, 1-hydroxy-1'-hydroperoxy dicyclohexyl peroxide; t-butyl peroxyisopropyl carbonate; 2,5-dimethyl-2,5-bis (benzoylperoxy) hexane; t-butyl peroxyacetate; methyl ethyl ketone peroxides; di-t-butyl diperoxyphthalate and t-butyl peroxybenzoate. Methods for initiating polymerization with free radicals are well known to those skilled in the art (Borton, *Complexes in Free-radical Polymerization*, Elsevier, N.Y. (1988); Bamford and Tipper, eds., *Free-radical Polymerization*, Elsevier, N.Y. (1976); Bevington, *Radical Polymerization*, Academic Press, New York (1961)).

Particularly useful peroxy initiators are those that do not discolor, char, or burn the resulting polymerizate. Exemplary initiators are diisopropyl peroxydicarbonate and benzoyl peroxide.

The invention provides a solid support comprising one or more ligands immobilized to a polyol (allyl carbonate) polymer support. The invention also provides a polyol (allyl carbonate) solid support modified for attachment of a chemical moiety. The solid support can be, for example, a bead, fiber, flat surface, microfluidic device, molded device, machined device, container, multi-well container such as a multi-well plate, mass spectrometry sample holder, or tissue culture vessel.

The solid supports of the invention can be used for a variety of purposes where a solid support having clarity, low fluorescence, solvent resistance and the ability to be chemically modified to allow attachment of a chemical moiety is desired. For example, the solid support can be used for storage of organic compounds, for synthetic chemistry, for combinatorial chemistry, and the like. Exemplary uses for the solid support include synthesis of oligonucleotides, polypeptides, including antibodies, or combinatorial libraries of organic molecules.

Methods for synthesizing chemical compounds on solid phase are well known to those skilled in the art (see, for example, Mendonca and Xiao, *Med. Res. Rev.* 19:451–462 (1999); van Maarseveen, *Comb. Chem. High Throughput Screen.* 1:185–214 (1998); Andres et al., *Comb. Chem. High Throughput Screen.* 2:191–210 (1999); Sucholeiki, *Mol. Divers.* 4:25–30 (1998–1999); Ito and Manabe, *Curr. Opin. Chem. Biol.* 2:701–708 (1998); Labadie, *Curr. Opin. Chem. Biol.* 2:346–352 (1998); Backes and Ellman, *Curr. Opin. Chem. Biol.* 1:86–93 (1997); Kihlberg et al., *Methods Enzymol.* 289:221–245 (1997); Blackburn and Kates, *Methods Enzymol.* 289:175–198 (1997); Meldal, *Methods Enzymol.* 289:83–104 (1997); Merrifield, *Methods Enzymol.* 289:3–13 (1997); Thuong and Asseline, *Biochimie.* 67:673–684 (1985); Wang et al., *Science* 279:1712–1714 (1998)).

Methods for peptide synthesis and the production of peptide libraries are also well known to those skilled in the art (Fodor et. al., *Science* 251:767 (1991); Gallop et al., *J. Med. Chem.* 37:1233–1251 (1994); Gordon et al., *J. Med. Chem.* 37:1385–1401 (1994)). Methods for making antibodies and/or antibody libraries are well known to those skilled in the art (see Huse et al. (*Science* 246:1275–1281 (1989); Winter and Harris, *Immunol. Today* 14:243–246 (1993); Ward et al., *Nature* 341:544–546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

The invention also provides a polyol (allyl carbonate) solid support for use in a mass spectrometer, for example, as a sample holder. A solid support for mass spectrometers can be effected by devising a slide, tray or wells onto which a sample or multiple samples can be localized as a dry film, in solution, or attached via ionic, hydrophobic, or covalent interaction with the polyol (allyl carbonate) polymer or derivatized surface thereof. The slide, tray or collection of wells can be inserted into a sample chamber of a mass spectrometer for analysis of the sample. The polyol (allyl carbonate) polymer solid support for mass spectrometry is particularly useful for matrix assisted laser desorption/ionization-time of flight (MALDI-TOF) mass spectrometry.

The invention disclosed herein provides a polyol (allyl carbonate) polymer support for the construction of biochips, microwell plates, tissue culture vessels and solvent, reagent, and compound reservoirs that are solvent resistant and optically clear.

The invention also provides a method of generating a solid support having one or more ligands immobilized thereto, comprising immobilizing one or more ligands to a polyol (allyl carbonate) polymer support. For example, a plurality of ligands can be contacted at discrete locations on a solid support, such as wells in a multi-well plate, or in an array format. Thus, the solid support can be used to generate biochips containing arrays of biological ligands such as oligonucleotides or polypeptides.

The invention also provides a method for attaching a chemical compound to a solid support. The method includes the step of contacting a polyol (allyl carbonate) solid support modified for attachment of a chemical moiety with a first chemical moiety. The method can further include the step of contacting the solid support with a second chemical moiety. The method can even further include optionally repeating the addition of one or more chemical moieties to the solid support. It is understood that any desired chemical can be used in any desired order. For example, the second chemical moiety can be the same or different than the first chemical moiety. Similarly, any additional chemical moiety can be a new chemical moiety, or can be the same as a previously added chemical moiety. The chemical moieties can be added in any desired position on the solid support in any desired order, and such distribution of chemical moieties is particularly useful for generating a library of chemical compounds.

Individual chemical moieties can be attached directly to the solid support or can be coupled to a chemical moiety attached to the solid support. In such a case, the chemical moiety being added and the chemical moiety attached to the solid support contain reactive groups that allow the chemical moieties to be coupled covalently. Alternatively, the chemical moiety being added and the chemical moiety attached to the solid support can contain functional groups that allow attachment via noncovalent interactions, for example, ionic or hydrophobic interactions. As such, the solid support can be conveniently used for combinatorial synthesis, with different chemical moieties being coupled in discrete locations in unique or replicate combinations to generate a combinatorial library. Thus, the solid support of the invention can be used to generate one or more populations of ligands useful for proteomics and genomics analyses, including polypeptides and nucleic acids.

The ligands can be attached to the solid support through either covalent or noncovalent interactions. For example, a nucleic acid ligand can be bound via noncovalent interactions to a polyol (allyl carbonate) solid support modified to contain a positively charged group such as an amine. Thus, the invention provides a polyol (allyl carbonate) solid support modified for attachment of a molecule via noncovalent interactions, for example, modified to contain a hydrophobic functional group suitable for hydrophobic interactions or a positively or negatively charged functional group suitable for ionic interactions. Such groups on the solid support can also function as reactive groups for covalent coupling to a chemical moiety or ligand if the chemical moiety or ligand is reactive with the functional group.

Thus, the solid supports of the invention can be used to synthesize or couple a population of molecules, which can be used in various applications, including analytical or diagnostic devices, chemical storage or synthesis, combinatorial library synthesis, and the like. As used herein, the term population is intended to refer to a group of two or more different molecules. Populations can range from two to tens to hundreds to thousands, or even millions or billions or more molecules. For example, a population can contain about 3 or more, about 5 or more, about 7 or more, about 10 or more, about 15 or more, about 20 or more, about 30 or more, about 40 or more, about 50 or more, about 75 or more, about 100 or more, about 200 or more, about 500 or more, or even about 1000 or more molecules. A population can also contain about $10^4$ or more, about $10^5$ or more, about $10^6$ or more, about $10^7$ or more, about $10^8$ or more or about $10^9$ or more molecules, about $10^{10}$ or more molecules, about $10^{11}$ or more molecules, about $10^{12}$ or more molecules, or even greater numbers of molecules. As used herein, a "subset" when used in reference to a population refers to group of molecules that is less than all of the population.

A variety of methods can be used to modify the solid support for attachment of a chemical moiety. For example, as disclosed herein, hydroxide such as potassium hydroxide, sodium hydroxide and the like can be used to derivatize a polyol (allyl carbonate) solid support for attachment of a chemical moiety (see Example III). Other methods for modifying a solid support for attachment of a chemical moiety or ligand can be readily determined by those skilled in the art. Other methods suitable for modifying a polyol (allyl carbonate) include, but are not limited to, plasma phase modification and copolymerization of the polyol (allyl carbonate) with a reagent containing a reactive functionality.

For plasma phase modification, plasma is generated by processing gas into an excited state by application of radio waves under reduced pressure. The excited gas is characterized by high energy radicals and ions. Exposure of the plastic to the excited gas causes deposition of the gas molecules onto the surface of the plastic. For example, deposition of amines can be carried out in an atmosphere of ammonia gas. Plasma phase modification of plastics can be effected with commercially available equipment like that manufactured by Europlasma (Belgium).

In addition to modifying a polyl (allyl carbonate) polymer (as disclosed herein in Example III), a polyol (allyl carbonate) polymer can be copolymerized in the presence of a reagent that provides a functional group suitable for binding to a chemical moiety or ligand. For example, a polyol (allyl carbonate) polymer can be copolymerized with a reagent containing a reactive functionality such as an amine or carboxylic acid, which can function both for noncovalent interactions and covalent interactions with a chemically reactive moiety.

In addition, a polyol (allyl carbonate) having chemical properties suitable as desirable binding properties for a chemical moiety or ligand can also be used to generate a solid support. For example, inclusion of an allylic amine during polymerization can be used to generate an aminated polymer useful for binding a chemical moiety or ligand, such as a polypeptide or nucleic acid, or a cell. Similarly, other polyol (allyl carbonates) having desirable chemical properties can be used to generate a polymer suitable for a particular use.

The synthesis of oligonucleotides on solid phase supports has become routine in many laboratories with the introduction of automated synthesis instruments. These standard synthetic reactions can be used to prepare an array of oligonucleotides on the surface of a polyol (allyl carbonate) polymer. Initially, a linker is attached to the solid support using one of several bifunctional linkers such as mono-FMOC 1,6-diaminohexane or a long chain alkyl amine. This linker is coupled to the 3'-hydroxy group of a 5'DMT protected nucleotide. Synthesis of the oligonucleotide then proceeds using standard phosphoramidate chemistry (Gryaznov and Letsinger *Tetrahedron Lett.* 33:4127–4128 (1992); Beaucage and Iyer *Tetrahedron Lett.* 48:2223–2311 (1992)) or the phosphite triester method (Montserrat et al. *Tetrahedron* 50:2617–2622 (1994)) to generate an oligonucleotide on the surface of the polyol (allyl carbonate) polymer.

Owing to its transparency, the polyol (allyl carbonate) polymer can be used as a solid support for the synthesis of oligonucleotide biochips using light directed synthesis (McGall et al. *J. Amer. Chem. Soc.* 119:5081–5090 (1997)). Illumination of selected region of the polymer will cause the cleavage of the protecting group and allow extension of the oligonucleotide chain.

The chemical resistance of polyol (allyl carbonate) polymers allows both light directed synthesis and FMOC chemistry (Fields and Noble *Int. J. Peptide Protein Res.* 35:16 (1990)) to be used for the synthesis of peptides on a solid support. For example, using polymer with diamine derivatized surface, the exposed amine groups can be derivatized by coupling FMOC-1-amino-hexanoic-(1'-hydroxybenzotriazole) ester (HOBt-ester). Following removal of the FMOC group, nitroveratryloxycarbonyl (NVOC) protected β-alanine-HOBt-ester or other derivative can be added. Individual solutions of (HOBt)-activated esters of each of the amino acids naturally occurring in proteins can be prepared. Side chains can be protected with t-butyl ether for serine, threonine, and tyrosine; t-butyl ester can be used to protect aspartic acid and glutamic acid; t-butoxycarbonyl (t-Boc) for lysine, histidine, and tryptophan; 2,2,5,7,8-pentamethylchroman-6-sulfonyl (Pmc) for arginine; and trityl (Trt) for cysteine. Spatially directed deprotection of the NVOC-protected amino group can be accomplished by illumination using focused visible light. The addition of the (HOBt)-activated ester of NVOC protected amino acids are allowed to react with the entire surface of the substrate in two cycles.

The invention further provides a tissue culture vessel comprising a polyol (allyl carbonate) polymer. The tissue culture vessel can be a flask, tube, plate, such as a single or multi-well plate, microfluidic device, microcarrier bead, or any desired shape suitable for in vitro culture of cells. The tissue culture vessel is suitable for maintaining the viability and/or growth of a cell in culture. The cell can be a eukaryotic or prokaryotic cell.

If desired, the tissue culture vessel can be modified for attachment of a cell. The tissue culture vessel can be modified as described above, for example, by chemically modifying or derivatizing a polyol (allyl carbonate) polymer or by copolymerizing a polyol (allyl carbonate) polymer with a reagent providing a functionality suitable for attachment of a cell or a functionality suitable for further chemical modification for attachment of a cell.

In addition, a tissue culture vessel of the invention can be coated with various compounds to facilitate cell attachment. Modifications of a tissue culture vessel or coating of a vessel to facilitate cell attachment are well known to those skilled in the art (see, for example, Harrison and Rae, *General Techniques of Cell Culture*, Cambridge University Press, New York (1997)). For example, negatively charged surfaces are generally used for eukaryotic tissue culture applications to facilitate attachment of positively charged cells, whereas positively charged plates are used for bacteriological applications. In addition, the tissue culture vessels of the invention can be coated with fibronectin, collagen, and the like, to facilitate the attachment of cell types that adhere to such compounds. Furthermore, a tissue culture vessel or other solid support of the invention can be modified for attachment of antibodies that can be used to bind specific cell types.

The invention additionally provides a method for generating a polyol (allyl carbonate) solid support by polymerizing a prepolymer of polyol (allyl carbonate), thereby generating a polyol (allyl carbonate) solid support. As described above, the use of a prepolymer can be advantageously used to minimize shrinkage during polymerization of a polyol (allyl carbonate). Use of a prepolymer can be useful in obtaining desirable characteristics of the polyol (allyl carbonate) solid support.

The invention also provides a microfluidic device comprising a polyol (allyl carbonate) polymer that can be used with aqueous or organic fluids. The devices can be machined or molded to include microchannels and wells and can optionally incorporate electrical connections. The surface of the microchannels and wells can be chemically modified to allow the attachment of chemical moieties or for modification of surface chemical properties including, but not limited to, hydrophobicity, ionic charge, and electroosmotic potential. Such modifications can similarly be included in any of the solid supports of the invention. The surface of the microchannels and wells can be chemically modified to alter the interaction of chemical moieties with the polyol (allyl carbonate) polymer as with the migration of chemical moieties in an electric field along the length of a microchannel.

Microfluidic devices, their applications, and standard manufacturing methods used for microfluidic devices have been described previously (Becker and Gartner, *Electrophoresis* 21:12–26 (2000); Freemantle, *Chem. Eng. News* 77:27–36 (1999); Voldman et al., *Ann. Rev. Bioengineer* 1:401–425 (1999); Chován and Guttman, *Trends Biotechnol.* 20:116–122 (2002); DeWitt, *Curr. Opin. Chem. Biol.* 3:350–356 (1999); Krishnan et al., *Curr. Opin. Biotechnol.* 12:92–98 (2001); Manz, ed., *Microsystem Technology in Chemistry and Life Sciences*, Springer-Verlag, New York (1999); Koch et al., *Microfluidic Technology and Applications*, Research Studies Press Limited, Tauton, Somerset, England (1999), and references cited therein). One skilled in the art can readily determine various applications of a polyol (allyl carbonate) polymer as a microfluidic device.

As used herein, the term "microchannel" refers to a channel less than 1 mm in width and 1 mm in depth. Microchannels can range in width or depth of 1 mm or less, 500 µm or less, 200 µm or less, 100 µm or less, 50 µm or less, 20 µm or less, 10 µm or less, 5 µm or less, 1 µm or less, or even smaller dimensions. Microchannels can have planar or curved walls and can be formed by molding, casting, micromachining, ablation, lithography, or any other method known to those skilled in the art.

As used herein, the term "microfluidic device" is intended to refer to devices with one or more microchannels used for the transfer or storage of a fluid. Microfluidic devices can optionally be used in conjunction with pumps, valves, electric currents, wells, mixers, or analytical detection systems.

Thus, the invention also provides a microfluidic device comprising a polyol (allyl carbonate) polymer solid support having one or more microchannels and one or more wells. The microfluidic device can be any desired composition of polyol (allyl carbonate), as disclosed herein, for example, diethylene glycol bis (allyl carbonate) of various percent composition. The microchannels can be formed by laser ablation (see Example VI). The microchannels can also be formed by molding or casting.

If desired, the microfluidic device can contain one or more ligands immobilized in the microchannels, as described above.

The microfluidic device can be modified to contain chemical functional groups with desirable chemical properties such as reactive groups, ionic, polar, hydrophobic, aromatic, or any desirable chemical property. For example, the chemical functional group can comprise an amine group, an alkyl group, a hydroxyl group, an aromatic group, a carboxylate group, or any desired chemical functionality.

It is understood that modifications which do not substantially affect the activity of the various embodiments of this invention are also provided within the definition of the invention provided herein. Accordingly, the following examples are intended to illustrate but not limit the present invention.

EXAMPLE I

Stability of Diethylene Glycol Bis(allyl carbonate) Polymer in Solvents

This example describes the stability of diethylene glycol bis(allyl carbonate) polymer in various solvents.

Pre-weighed 2 cm×2 cm chips of diethylene glycol bis (allyl carbonate) polymer were submerged in various solvents or reagents commonly used in solid phase oligonucleotide and peptide synthesis for 3 hours at room temperature. The solvents used were dimethylformamide (DMF), dichloromethane (DCM), methanol, acetonitrile, acetone, 20% piperidine in DMF, 1% trifluoroacetic acid (TFA) in DCM, and water. A chip unexposed to any solvent was used as a control. The chips were removed from the solution and wiped dry. The change in weight and % transmittance of light at various wavelengths was then determined for each chip. The results observed at 400 nm are shown in Table 1.

TABLE 1

Effect of Solvents on Diethylene Glycol Bis(allyl carbonate) Polymer

| Condition | Δ% weight | Δ% T (400 nm) |
|---|---|---|
| Control | <0.3 | <3 (S.D. 3) |
| DMF | <0.3 | 3.6 |
| DCM | 3.4 | 6.5 |
| Methanol | <0.3 | 6.1 |
| Acetonitrile | 0.5 | 3.5 |
| Acetone | <0.3 | <3 |
| 20% piperidine/DMF | <0.3 | <3 |
| 1% TFA/DCM | 3.0 | 6.0 |
| water | <0.3 | <3 |

As shown in Table 1, there was no significant change in weight or percent transmittance at 400 nm. Similarly, there was no significant change in percent transmittance at 280, 300, 320, 340, 360, 380 or 600 nm.

These results show that the polyol (allyl carbonate) polymer diethylene glycol bis(allyl carbonate) is resistant to a variety of solvents and maintains clarity after exposure to a variety of solvents.

EXAMPLE II

Intrinsic Fluorescence of Diethylene Glycol Bis (allyl carbonate) Polymer

This example describes the intrinsic fluorescence properties of diethylene glycol bis(allyl carbonate) polymer.

The emission spectrum of a 12.5 cm×8.5 cm×0.2 cm sheet of diethylene glycol bis(allyl carbonate) polymer was measured in a Molecular Devices SPECTRAmax Gemini XS spectrofluorometer (Molecular Devices; Sunnyvale Calif.) over the wavelength range of 300 nm to 600 nm with an excitation wavelength of 260 nm. This spectrum was compared to the spectrum generated from an inverted Corning-CoStar polystyrene plate (Corning; Acton Mass.). Polystyrene showed emission peaks at 330 nm and 510 nm. Diethylene glycol bis(allyl carbonate) polymer showed no detectable fluorescence in the range of 300 nm to 600 nm.

These results show that the polyol (allyl carbonate) polymer diethylene glycol bis(allyl carbonate) exibits low intrinsic fluorescence.

EXAMPLE III

Dervitization of Diethylene Glycol Bis(allyl carbonate) Polymer

This example describes the derivatization of diethylene glycol bis(allyl carbonate) polymer at discrete locations.

The surface of a 12.5 cm×8.5 cm×0.2 cm sheet of polymerized diethylene glycol bis(allyl carbonate) was covered with cellophane tape having 96 holes of 0.8 cm diameter distributed in an 8×12 array. This sheet was floated, tape side down, in a bath of 45% (w/v) aqueous potassium hydroxide for three hours at room temperature. The sheet was washed extensively with water and the tape was removed. Hydrolysis of carbonate bonds in the polymer was demonstrated by the formation of water beads on the surface of the sheet in locations corresponding to the 8×12 array.

These results show that the polyol (allyl carbonate) polymer diethylene glycol bis(allyl carbonate) can be derivatized at discrete locations. Such derivatized locations are suitable for attachment of chemical moieties on a solid support.

EXAMPLE IV

Coupling of Amino Acid to Diethylene Glycol Bis (allyl carbonate) Polymer

This example describes attachment of a chemical moiety to derivatized diethylene glycol bis(allyl carbonate) polymer.

1 mmol FMOC-Ser(trt)-OH was dissolved in a minimum volume of dry DMF. To this solution, 1 mmol dicyclohexylcarbodiimide (DCC) in dry DCM was added to the amino acid solution and incubated at 0° C. for 30 min. Hydroxide treated diethylene glycol bis(allyl carbonate) polymer was submerged in a minimum amount of dry DMF, and the amino acid solution was added. 0.1 mmol dimethylaminopyridine (DMAP) was added with 0.1 g molecular sieves. The reaction was covered and allowed to stand 1 hr at room temperature with occasional swirling. The derivatized polymer was washed with an excess DMF.

Alternatively, 1 mmol FMOC-Ser(trt)-OH was dissolved in a minimum volume of dry DMF. To this solution, 1 mmol DCC in dry DCM was added to the amino acid solution and incubated at 0° C. for 30 min. Hydroxide treated diethylene glycol bis (allyl carbonate) polymer was activated in 20 mL dry tetrahydrofuran (THF) containing 0.25 mmol diimidazole carbonyl, 75 mmol dimethylaminopyridine (DMAP) and about 0.1 g molecular sieves for 3 hours at room temperature. The activated slide was washed with dry THF and dry DMF and was submerged in a minimum amount of dry DMF, to which the amino acid solution was added. 0.1 mmol DMAP was added with 0.1 g molecular sieves. The reaction was covered and allowed to stand 1 hr at room temperature with occasional swirling. The derivatized polymer was washed with an excess DMF.

Coupling was verified by removal of fluorenylmethyloxycarbonyl (FMOC) with 20% piperidine in DMF and detection of the primary amine using the Kaiser test. The Kaiser test was carried out by preparation of three solutions. Solution 1 consists of 5 g ninhydrin in 100 ml ethanol. Solution 2 consists of 80 g liquified phenol in 20 ml ethanol. Solution 3 is a mixture of 2 ml of 1 mM aqueous sodium cyanide in 98 ml pyridine. The active reagent was formed by mixing equal volumes of each of solutions 1 to 3 and adding the resulting mixture dropwise to the test sample. The sample exposed to the active reagent was dried at 110° C. for 10 minutes. The presence of a primary amine was confirmed by the appearance of a blue coloring after 5 minutes at 120° C.

These results show that a chemical moiety can be attached to derivatized diethylene glycol bis(allyl carbonate).

EXAMPLE V

Bromination of Diethylene Glycol Bis(allyl carbonate) Polymer

This example describes the attachment of a chemical moiety to a derivatized diethylene glycol bis(allyl carbonate) polymer.

Hydroxide treated diethylene glycol bis(allyl carbonate) polymer is submerged in a solution of 200 mM carbon tetrabromide in DCM for 15 hours at room temperature with 100 mM triphenylphosphine. The brominated polymer is washed extensively with DMF. The coupling of the amine is carried out by addition of 1 mmol FMOC-propylene diamine added in a minimum amount of DCM and allowed to stand covered for 3 hours at room temperature. Coupling is verified following removal of FMOC with 20% piperidine in DMF using the Kaiser test.

EXAMPLE VI

Laser Ablation of Diethylene Glycol bis(allyl carbonate) Polymer

This example describes the machining of microchannels in diethylene glycol bis (allyl carbonate) polymer.

Microchannels 20 μm wide were laser ablated into diethylene glycol bis (allyl carbonate) polymer slides (1"×3"×1/16") using an Electro Scientific, Inc. (Portland, Oreg.) 4440 Laser Micromachining System. This system used a solid state pulsed diode laser adjusted to emit light at 266 nm. Pulsewidths of 15–20 ns were used to write a test pattern from an AutoCAD file without thermal degradation of the surrounding regions.

This example shows that a diethylene glycol bis (allyl carbonate) polymer can be laser ablated to form microchannels. A diethylene glycol bis (allyl carbonate) polymer, on which microchannels can be formed, can thus be used as a microfluidic device.

EXAMPLE VII

Preparation of a Diethylene Glycol Polymer Multiwell Plate

A two-piece mold for a 96-well multiwell plate was cast in mold making silicone (KE1310ST, Shin-Etsu, Akron, Ohio) using a commercially available polystyrene 96-well plate as the template. The silicone mold was lightly coated with silicone mold release, clamped together with aluminum brackets and filled with diethylene glycol bis (allyl carbonate) containing 3% benzoyl peroxide through a port carved into the bottom of the mold. Air was vented from slits carved into the top of the mold. The assembly was gradually heated to 90° C. over 8 hrs to effect the polymerization of the diethylene glycol. The hardened diethylene glycol bis (allyl carbonate) polymer 96-well plate was removed from the silicone mold following cooling of the assembly to room temperature.

This example shows that diethylene glycol bis (allyl carbonate) can be used to mold a solid support in a 96-well format.

EXAMPLE VIII

Preparation of a Diethylene Glycol Bis(Allyl Carbonate) Polymer CD

A nickel music compact disc (CD) mold was affixed to a 10"×10"×¼" tempered glass plate using silicone adhesive. Silicone o-rings with Shore hardness ratings of 40 were used to form the center opening of the CD and outer perimeter of the CD mold by sandwiching the o-rings between the nickel mold and a second 10"×10"×¼" plate of tempered glass. The mold was held together with binder clips. Diethylene glycoal bis (allyl carbonate) containing 3% benzoyl peroxide was injected into the cavity formed between the two glass plates, and air was vented through a hypodermic needle. The assembly was heated to 90° C. over 8 hrs to effect polymerization of the diethylene glycol bis (allyl carbonate). The hardened diethylene glycol bis (allyl carbonate) polymer CD was removed from the mold following cooling of the assembly to room temperature. Micron-sized wells molded into the surface of the diethylene glycol bis (allyl carbonate) polymer CD was verified by microscopy.

This example shows that diethylene glycol bis (allyl carbonate) can be molded into a CD format.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

I claim:

1. A solid support comprising one or more ligands immobilized to a polyol (allyl carbonate) polymer solid support.

2. The solid support of claim 1, wherein said ligands comprise a nucleic acid or a polypeptide.

3. The solid support of claim 1, wherein said polyol (allyl carbonate) polymer is diethylene glycol bis(allyl carbonate) or a copolymer comprising greater than about 10% diethylene glycol bis(allyl carbonate).

4. The solid support of claim 1, wherein said polymer is generated by polymerizing a prepolymer of polyol (allyl carbonate).

5. A multi-well plate, comprising a polyol (allyl carbonate) polymer solid support having a plurality of wells.

6. The multi-well plate of claim 5, wherein said polyol (allyl carbonate) is diethylene glycol bis(allyl carbonate) or a copolymer comprising at least about 10% diethylene glycol bis(allyl carbonate).

7. The multi-well plate of claim 5, wherein said polymer is generated by polymerizing a prepolymer of polyol (allyl carbonate), thereby generating a polyol (allyl carbonate) solid support.

8. A multi-well plate for attachment of a chemical moiety, comprising a polyol (allyl carbonate) polymer solid support having a plurality of wells, said wells being modified for attachment of a chemical moiety.

9. The multi-well plate of claim 8, wherein said polyol (allyl carbonate) is diethylene glycol bis(allyl carbonate) or a copolymer containing at least about 10% diethylene glycol bis(allyl carbonate).

10. The multi-well plate of claim 8, wherein said polymer is generated by polymerizing a prepolymer of polyol (allyl carbonate).

11. A solid support, comprising a polyol (allyl carbonate) polymer solid support modified for attachment of a chemical moiety.

12. The solid support of claim 11, wherein said polyol (allyl carbonate) is diethylene glycol bis(allyl carbonate) or a copolymer containing at least about 10% diethylene glycol bis(allyl carbonate).

13. The solid support of claim 11, wherein said solid support is selected from the group consisting of a bead, fiber, flat surface, microfluidic device, molded device, machined device, container, multi-well container, and mass spectrometry sample holder.

14. The solid support of claim 11, wherein said polymer is generated by polymerizing a prepolymer of polyol (allyl carbonate).

15. A tissue culture vessel comprising a polyol (allyl carbonate) polymer, wherein a surface of said tissue culture vessel is modified for attachment of a cell.

16. The tissue culture vessel of claim 15, wherein said tissue culture vessel is selected from the group consisting of a flask, tube, plate, and microfluidic device.

17. The tissue culture vessel of claim 16, wherein said plate is a multi-well plate.

18. The tissue culture vessel of claim 15, wherein said polyol (allyl carbonate) is diethylene glycol bis(allyl carbonate) or a copolymer containing at least about 10% diethylene glycol bis(allyl carbonate).

19. The tissue culture vessel of claim 15, wherein said polymer is generated by polymerizing a prepolymer of polyol (allyl carbonate).

20. A method of generating a solid support having one or more ligands immobilized thereto, comprising immobilizing one or more ligands to a polyol (allyl carbonate) polymer solid support.

21. The method of claim 20, wherein said ligands comprise a nucleic acid or a polypeptide.

22. The method of claim 20, wherein said polyol (allyl carbonate) polymer is diethylene glycol bis(allyl carbonate) or a copolymer containing greater than about 10% diethylene glycol bis(allyl carbonate).

23. The method of claim 20, wherein said polymer is generated by polymerizing a prepolymer of polyol (allyl carbonate).

24. A method for attaching a chemical compound to a solid support, comprising:

(a) contacting the polyol (allyl carbonate) polymer solid support of claim 11 with a first chemical moiety.

25. The method of claim 24, further comprising the step of:

(b) contacting said solid support with a second chemical moiety.

26. The method of claim 25, further comprising the step of optionally repeating step (b) one or more times with a chemical moiety.

27. The method of claim 24, wherein said solid support is a multi-well plate and the wells of said multi-well plate are modified for attachment of a chemical moiety.

28. The method of claim 24, wherein said chemical moiety comprises a nucleic acid or a polypeptide.

29. The method of claim 24, wherein said polymer is generated by polymerizing a prepolymer of polyol (allyl carbonate).

30. The method of claim 24, wherein said polyol (allyl carbonate) polymer is diethylene glycol bis(allyl carbonate) or a copolymer comprising at least about 10% diethylene glycol bis(allyl carbonate).

31. A microfluidic device comprising a polyol (allyl carbonate) polymer solid support having one or more microchannels and one or more wells.

32. The microfluidic device of claim 31, wherein the microchannels are formed by laser ablation.

33. The microfluidic device of claim 31, wherein the microchannels are formed by molding or casting.

34. The microfluidic device of claim 31, comprising one or more ligands immobilized in the microchannels.

35. The microfluidic device of claim 31, microfluidic device is modified to contain a chemical functional group selected from the group consisting of an amine group, an alkyl group, a hydroxyl group, an aromatic group, and a carboxylate group.

36. The microfluidic device of claim 31, wherein said polyol (allyl carbonate) polymer is diethylene glycol bis (allyl carbonate) or a copolymer comprising greater than 10% diethylene glycol bis (allyl carbonate).

* * * * *